United States Patent [19]

Bolich, Jr.

[11] Patent Number: 4,834,968
[45] Date of Patent: May 30, 1989

[54] HAIR STYLING MOUSSE

[75] Inventor: Raymond E. Bolich, Jr., Mainville, Ohio

[73] Assignee: The Procter & Gamble Co., Cincinnati, Ohio

[21] Appl. No.: 223,722

[22] Filed: Jul. 21, 1988

Related U.S. Application Data

[63] Continuation of Ser. No. 836,794, Mar. 6, 1986, abandoned, which is a continuation-in-part of Ser. No. 741,770, Jun. 6, 1985, abandoned.

[51] Int. Cl.$^4$ .............................. A61K 7/11; A61K 9/12
[52] U.S. Cl. ................................. 424/47; 424/DIG. 1
[58] Field of Search ........................................... 424/47

[56] References Cited

U.S. PATENT DOCUMENTS

| | | | |
|---|---|---|---|
| 3,208,911 | 9/1965 | Oppliger | 167/87 |
| 3,655,865 | 4/1972 | Murphy | 424/45 |
| 3,912,666 | 10/1975 | Spitzer et al. | 260/2.5 E |
| 4,264,586 | 4/1981 | Callingham et al. | 424/68 |
| 4,268,499 | 5/1981 | Keil | 424/68 |

FOREIGN PATENT DOCUMENTS

| | | |
|---|---|---|
| 2943521 | 5/1981 | Fed. Rep. of Germany . |
| 992087 | 5/1965 | United Kingdom . |
| 1589230 | 5/1981 | United Kingdom . |

OTHER PUBLICATIONS

Billek, Doris E., "Aerosol Foam and Mousse Preparations in Europe", *Cosmetics & Toiletries*, vol. 99, (Sep. 1984), pp. 57–60, 62–67–Mousse Compositions.

*Primary Examiner*—Dale R. Ore
*Attorney, Agent, or Firm*—David L. Suter; Douglas C. Mohl; Steven J. Goldstein

[57] ABSTRACT

Aqueous aerosol mousse compositions are disclosed which contain a silicone material dissolved in the aerosol propellant phase. Such compositions are not only easily processed but also provide for better dry combing than is obtainable if the silicone material is dispersed in the aqueous phase.

7 Claims, No Drawings

HAIR STYLING MOUSSE

CROSS REFERENCE TO RELATED APPLICATION

This is a continuation of application Ser. No. 836,794, filed on Mar. 6, 1986, now abandoned which is a continuation-in-part application of my copending application Ser. No. 741,770, filed June 6, 1985, now abandoned.

TECHNICAL FIELD

The present invention relates to aqueous hair stying aerosol mousse compositions which provide excellent set hold as well as combing ease.

BACKGROUND OF THE INVENTION

The desire to have hair (human or other animal) retain a particular shape or configuration is one that is widely held. Approaches taken can either involve permanent alteration of the hair or a temporary alteration. The former involves the use of chemical agents to react with the hair in order to achieve the desired effect. This process can be carried out at either room or elevated temperature.

The temporary set to hair is, as the term indicates, a temporary arrangement which can be removed by water or by shampooing. The materials used to provide the set have generally been resins or gums. The temporary set compositions have taken the form of gels, lotions and sprays as well as others. The compositions are applied most often to hair dampened with water, combined or by other means spread through the hair and let dry. The set given will vary depending on the materials used.

In recent years a form of a temporary set has been achieved by means of an aerosol foam—a mousse. This form, which can easily be worked through the hair, can provide a set comparable to that given by a gel or a lotion. These products are generally applied to the user's hand and worked through the hair.

The conventional hair styling mousse, which got its start in Europe, generally utilizes a water soluble polymer, water, possibly a conditioning agent, an emulsifier, aesthetic agents and the propellant. The conditioning agents used have included silicone type materials. Such formulations are disclosed in Billek, Doris E., "Aerosol Foam and Mousse Preparations in Europe", Cosmetics & Toiletries, Vol. 99 (September 1984), 57-60, 62-67.

The present invention involves the use of high molecular weight silicone materials in styling mousses. The formulae disclosed in Billek, while containing silicone type agents, do not disclose high molecular weight materials or any materials dissolved in the propellant phase. A reference disclosing a variety of materials dissolved in the propellant phase prior to filling the container is Offenlegungsschrift DE 29 43 521, May 5, 1971. This reference does not however disclose high molecular weight silicone materials either. Such materials are however disclosed in non-aerosol hair conditioning formulations in U.S. Pat. No. 4,387,090, June 7, 1983 to R. E. Bolich, Jr.

The present invention has found that combining the silicone material with the propellant eliminates the need to mill the material, which would probably be necessary if it were to be combined with the aqueous phase. Additionally unexpected results have been found in hair conditioning (dry combing) and set hold when the material is in the propellant phase.

Therefore it is a purpose of the present invention to provide a superior hair styling mousse.

It is a further object of the present invention to provide a hair styling mousse employing a high molecular weight silicone material dissolved in the propellant phase.

These and other objects of the present invention will become readily apparent from the detailed description which follows.

All percentages and ratios used herein are by weight unless otherwise specified.

SUMMARY OF THE INVENTION

The present invention relates to aerosol compositions comprising water, a hair setting polymer soluble/dispersible in an aqueous phase and a solution of a high molecular weight silicone hair conditioning agent in a propellant phase.

DETAILED DESCRIPTION OF THE INVENTION

The essential as well as optional components are specified below.

Water

Water, preferably distilled or deionized, is the first essential component of the present invention. The water is generally present at a level of from about 55% to about 94%, preferably from about 80% to about 90% of the total composition.

Polymer

The polymer useful in the present compositions is any polymer soluble or colloidally dispersible in the aqueous phase, the polymer water is the only solvent in the aqueous phase, the polymer should be soluble or dispersible in water; if an optional cosolvent such as ethanol is present the polymer should be soluble or dispersible in the combined solvent system). Solubility/dispersibility is determined at ambient conditions (e.g., temperature about 25° C. and atmospheric pressure). Suitable types of polymers include anionic, nonionic, amphoteric and cationic. Specific polymers include polyvinylpyrrolidone (PVP), copolymers of (PVP) and methylmethacrylate, copolymers of PVP and vinylacetate (VA), polyvinyl alcohol (PVA), copolymers of PVA and crotonic acid, copolymers of PVA and maleic anhydride, hydroxypropyl cellulose, hydroxypropyl guar gum, sodium polystyrene sulfonate, PVP/ethylmethacrylate/methacrylic acid terpolymer and octylacrylamide/acrylate/butylaminoethyl methacrylate copolymers. PVP and PVP copolymers with other monomers are preferred.

Mixtures of polymers may also be used. With certain of the polymers it may be necessary to neutralize some acidic groups to promote solubility/dispersibility (e.g., PVA/crotonic acid).

The polymer(s) is used at a level of from about 0.5% to about 10%, preferably from about 1% to about 6% of the total composition. The mass average molecular weight of the polymer is not critical but is generally in the range of from about 2,000 to about 2,000,000.

Propellant

The agent responsible for expelling the other materials from the container and forming the mousse character is a propellant.

The propellant gas can be any liquefiable gas conventionally used for aerosol containers. Preferably the density of the propellant or mixture thereof is less than 1 so that pure propellant is not emitted from the container. Examples of materials that are suitable for use as propellants are trichlorofluoromethane, dichlorodifluoromethane, dichlorotetrafluoroethane, monochlorodifluoromethane, trichlorotrifluoroethane, dimethylether, propane, η-butane and isobutane, used singly or admixed. The hydrocarbons, particularly isobutane, used singly or admixed with other hydrocarbons, are preferred due to their densities being less than 1.

The amount of the propellant gas is governed by normal factors well known in the aerosol art. For mousses the level of propellant is generally from about 5% to about 20%, preferably from about 7% to about 15% of the total composition. If a propellant such as dimethylether utilizes a vapor pressure suppressant (e.g., trichloroethane or dichloromethane) the amount of suppressant is included as part of the propellant.

High Molecular Weight Silicone Material

The agent providing hair conditioning (e.g., dry hair combing) is a high molecular weight silicone material. References disclosing such silicones are U.S. Pat. No. 4,152,416, May 1, 1979 to Spitzer, et al.; *Silicon Compounds*, distributed by Petrarch Systems; and Noll, Walter, *Chemistry and Technology of Silicones*, New York: Academic Press 1968. Also describing high molecular weight silicone materials are General Electric Silicone Rubber Product Data Sheets SE 30, SE 33, SE 54 and SE 76. These references are incorporated herein by reference.

Because of the ready availability of equipment and the simplicity of the method, commercial manufacturers generally characterize high molecular weight silicones by their viscosity or in some cases by a penetration value. High molecular weight silicone materials denotes polydiorganosiloxanes having a viscosity of at least 100,000 centistokes, preferably from about $10^5$ to about $15 \times 10^6$. Specific examples include polydimethylsiloxane, methylphenyl-diphenyl siloxane copolymer, (polydimethylsiloxane) (methylvinylsiloxane) copolymer and poly(dimethylsiloxane) (diphenyl) (methylvinylsiloxane) copolymer and mixtures of these agents. The silicon material is generally present at a level of from about 0.05% to about 2%, preferably from about 0.1% to about 1% by weight of the total composition.

Optional Components

The aerosol mousses herein can contain a variety of nonessential, optional components suitable for rendering such compositions more acceptable. Such conventional optional ingredients are well known to those skilled in the art, e.g., emulsifiers such as anionics (e.g. sodium alkyl sulfate) and nonionics (amine oxides); preservatives such as benzyl alcohol, ethyl paraben, propyl paraben and imidazolidinyl urea; cationic emulsifiers/conditioners such as cetyl trimethyl ammonium chloride, stearyldimethyl benzyl ammonium chloride, and di(partially hydrogenated tallow) dimethylammonium chloride; thickeners and viscosity modifiers such as a diethanolamide of a long chain fatty acid; block polymers of ethylene oxide and propylene oxide such as Pluronic F88 offered by BASF Wyandotte, fatty alcohols such as cetearyl alcohol, sodium chloride, sodium sulfate, and ethyl alcohol; pH adjusting agents such as critic acid, succinic acid, sodium hydroxide and triethanolamine; coloring agents such as any of the FD&C or D&C dyes; hair oxidizing (bleaching) agents such as hydrogen peroxide, perborate salts and persulfate salts; hair reducing agents such as the thioglycolates; perfume oils; chelating agents such as ethylenediamine tetracetic acid; and, among many other agents, polymer plasticizing agents such as glycerin and propylene glycol. These optional materials are generally used individually at a level of from about 0.01% to about 10%, preferably from about 0.5% to about 5% by weight of the total composition.

Another optional component preferred for use herein is a low viscosity silicone fluid to be used along with the high molecular weight silicone material in the propellant phase. Such materials may be either a polyalkyl siloxane, a polyaryl siloxane, a polyalklaryl siloxane or a polyether siloxane copolymer. These materials preferably have a viscosity of from about 5 to about 10,000 centistokes, most preferably from about 100 to about 1,000 centistokes, at 25° C. The agent is preferably used at a level of from about 0.1% to about 1% by weight of the total composition.

METHOD OF MANUFACTURE

The method of preparing the aerosol compositions of the present invention follows conventional aerosol filling procedures. The water soluble or dispersible materials (not including the silicone material) are mixed with water to from a 'concentrate'. This concentrate, in an appropriate amount, is placed into an aerosol container. The container is then fitted with a valve, subjected to a vacuum to rid the container of air and sealed with the valve "crimped" in place. The silicone material is then mixed with the propellant fluid and the propellant/silicone mixture is filled into the container through the valve.

INDUSTRIAL APPLICABILITY

The present compositions are emitted from the aerosol container as a foam which is then worked through the hair with the fingers or a hair styling implement and either left on the hair or rinsed out.

The following Examples further describe and demonstrate the preferred embodiments within the scope of the present invention. The Examples are given solely for the purpose of illustration and are not to be constructed as limitations of the present invention as many variations thereof are possible without departing from its spirit and scope.

EXAMPLE 1

The following composition representative of the present invention was prepared.

| Component | Wt. % |
|---|---|
| LUVISKOL K-60[1] (45% active in water) | 6.11 |
| Adogen 470[2] (75% active in ethanol) | 0.20 |
| Schercamox CMA[3] (38% active in water) | 0.38 |
| Preservative | 0.03 |
| Propellant A-46[4] | 10.00 |
| Silicone Gum (GE SE-76)[5] | 0.17 |
| Dimethicone Fluid | 0.33 |
| (350 Centistokes at 25° C.) | |

-continued

| Component | Wt. % |
|---|---|
| Water | qs 100.00% |

[1] Offered by BASF Wyandotte having molecular weight of about 300,000
[2] Di(partially hardened tallow) dimethyl ammonium chloride offered by Sherex
[3] Dihydroxyethyl cocamine oxide offered by Scher Chemical Company
[4] (20%/78%/2%) Propane/isobutane/$\eta$-butane offered by Phillips Petroleum Company
[5] Silicone gum offered by General Electric

EXAMPLE II

| Component | Wt. % |
|---|---|
| Gafquat 734[1] (50% active in ethanol) | 5.50 |
| Adogen 470 (75% active in water) | 0.20 |
| Barlox 12[2] (30% active in water) | 0.83 |
| Preservative | 0.03 |
| [ Propellant A-46 | 10.00 ] |
| [ Silicone Gum (GE SE-76) | 0.08 ] |
| [ Dimethicone Fluid (350 Centistokes) | 0.17 ] |
| Water | qs 100.00% |

[1] Copolymer of vinylpyrrolidone and dimethyl aminoethylmethacrylate reacted with dimethyl sulfate from GAF
[2] Dimethyl cocamine oxide offered by Lonza, Inc.

The following is another composition representative of the present invention which was prepared.

| Component | Wt. % |
|---|---|
| Ultrahold 8[1] (50% active in ethanol) | 5.500 |
| Barlox 12 (30% active in water) | 0.83 |
| SDA 40 Ethyl Alcohol | 10.000 |
| [ Propellant A-46 | 10.000 ] |
| [ Silicone Gum (GE SE-76) | 0.125 ] |
| [ CETETH-2 | 0.050 ] |
| Water | qs 100.000% |

[1] Neutralized form of the terpolymer of acrylic acid, ethyl acrylate and N—tertiary butyl acrylamide offered by Ciba-Geigy, Inc.

EXAMPLE III

The following is another composition of the present invention which was prepared.

EXAMPLE IV

The following composition representative of the present invention is prepared.

| Component | Wt. % |
|---|---|
| Polyvinylpyrrolidone K-30[1] | 4.00 |
| Ditallowdimethyl Ammonium Chloride | 0.25 |
| Polyethylene Glycol 6000 Disterate | 0.80 |
| Propylene Glycol | 3.00 |
| Preservative | 0.03 |
| [ Propellant A-46 | 15.00 ] |
| [ Silicone Gum (GE SE-30) | 0.70 ] |
| Water | qs 100.00% |

[1] Offered by GAF having molecular weight of about 50,000

EXAMPLE V

The following composition of the present invention is prepared.

| Component | Wt. % |
|---|---|
| LUVISKOL VA 73E[1] (50% active in ethanol) | 3.00 |
| Sodium Coconut Alkyl Sulfate | 0.50 |
| SDA 40 Ethyl Alcohol | 15.00 |
| Glycerin | 0.80 |
| Dow Corning 193 Surfactant[2] | 0.20 |
| [ Propellant A-46 | 7.00 ] |
| [ Silicone Gum (GE SE-76) | 0.18 ] |
| Water | qs 100.00% |

[1] Poly(vinylpyrrolidone/vinyl acetate) copolymer offered by BASF Wyandotte Corporation
[2] Copolyol nonionic surfactant offered by Dow Corning In the above Examples the materials within the bracket in each Example were mixed together and filled into the aerosol container through the valve.

What is claimed is:

1. An aerosol hair styling mousse composition comprising:
   (a) from about 0.5% to about 10% by weight of a hair setting polymer soluble or dispersible in the aqueous phase of the hair styling mousse composition;
   (b) from about 0.05% to about 2% by weight of a high molecular weight silicone material which is a polydiorganosiloxane having a viscosity of from about $10^5$ to about $15 \times 10^6$ centistokes;
   (c) from about 5% to about 20% by weight of an aerosol propellant which is a liquifiable gas conventionally used in aerosol containers for expelling the materials from the container and forming the mousse character of the hair styling mousse composition; and
   (d) the remainder water; wherein said silicone material is dissolved in said propellant prior to said propellant being put into an aerosol container.

2. An aerosol composition according to claim 1 wherein the propellant is selected from the group consisting of trichlorofluoromethane, dichlorodifluoromethane, dichlorotetrafluoroethane, monochlorodifluoromethane, trichlorotrifluoroethane, dimethyl ether, propane, isobutane, and n-butane.

3. An aerosol composition according to claim 2 wherein the hair setting polymer is selected from the group consisting of polyvinylpyrrolidone, copolymers of polyvinylpyrrolidone and methylmethacrylate, copolymers of polyvinylpyrrolidone and vinylacetate, polvinyl alcohol, copolymers of polyvinyl alcohol and crotonic acid, copolymers of polyvinyl alcohol and maleic anhydride, hydroxypropyl cellulose, hydroxypropyl guar gum, sodium polystyrene sulfonate, polyvinylpyrrolidone/ethlmethyacrylate/methacrylic acid terpolymer, and octylacrylamide/acrylate/butylaminoethyl methacrylate copolymers.

4. An aerosol composition according to claim 2 wherein the propellant is selected from the group consisting of propane, n-butane, and isobutane.

5. An aerosol composition according to claim 1 which in addition contains from about 0.1% to about 1% by weight of a low viscosity silicone fluid material selected from the group consisting of polyalkyl siloxane, polyaryl siloxane, polyalkylaryl siloxane, and polyether siloxane copolymer, and further having a viscosity of from about 5 to about 10,000 centistokes.

6. A method of styling hair by applying a composition according to claim 1 to said hair.

7. A method of styling hair by applying a composition according to claim 5 to said hair.

* * * * *